United States Patent [19]
Green

[11] Patent Number: 5,575,643
[45] Date of Patent: Nov. 19, 1996

[54] ORTHODONTIC TOOL

[76] Inventor: William F. Green, Rte. 5, Box 84, Fort Payne, Ala. 35967

[21] Appl. No.: 394,699

[22] Filed: Feb. 27, 1995

[51] Int. Cl.$^6$ .................................................. A61C 3/00
[52] U.S. Cl. .............................................. 433/3; 606/140
[58] Field of Search .................. 433/3, 4, 23; 606/163, 606/140, 141

[56] References Cited

U.S. PATENT DOCUMENTS

| | | | |
|---|---|---|---|
| 1,064,404 | 6/1913 | Walker | 433/4 |
| 1,531,898 | 3/1925 | Angle et al. | 433/3 |
| 2,125,404 | 8/1938 | Snyder | 606/148 |
| 2,447,474 | 8/1948 | Hammond | 128/319 |
| 2,561,286 | 7/1951 | Montgomery | 606/140 |
| 2,840,081 | 6/1958 | Moose | 606/140 |
| 2,840,082 | 6/1958 | Salvatore | 128/303 |
| 2,942,604 | 6/1960 | Gravlee, Jr. | 606/140 |
| 4,001,940 | 1/1977 | Cusato | 433/3 |
| 4,370,979 | 2/1983 | Erickson | 128/303 |
| 4,472,137 | 9/1984 | Barone | 433/3 |
| 4,474,555 | 10/1984 | Diamond | 433/3 |
| 4,669,979 | 6/1987 | Snead | 433/4 |
| 4,875,855 | 10/1989 | Beckett | 433/3 |
| 4,921,423 | 5/1990 | Kesling | 433/3 |
| 4,975,051 | 12/1990 | Kargas et al. | 433/3 |

FOREIGN PATENT DOCUMENTS 661084 7/1929 France.
1169630 7/1985 U.S.S.R..

Primary Examiner—Paul J. Hirsch
Attorney, Agent, or Firm—Hopkins & Thomas

[57] ABSTRACT

An orthodontic tool is described wherein an elastic band can be easily stretched into a triangular shape and attached over the hooks of an orthodontic apparatus attached within a mouth. The tool can be operated with a single hand and the rubber band can be stretched and placed over a first hook and then partially released from the tool. The second end of the rubber band is placed over a second hook in the mouth and the rubber band is completely released from the tool which is then removed from the mouth. The tool comprises two stationary L-shaped ends and one L-shaped end movable from the two stationary ends.

10 Claims, 2 Drawing Sheets

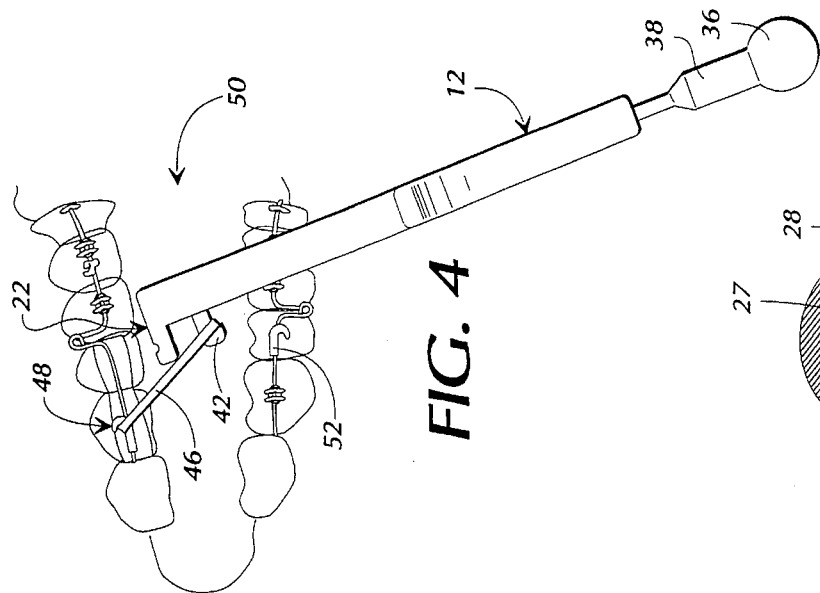
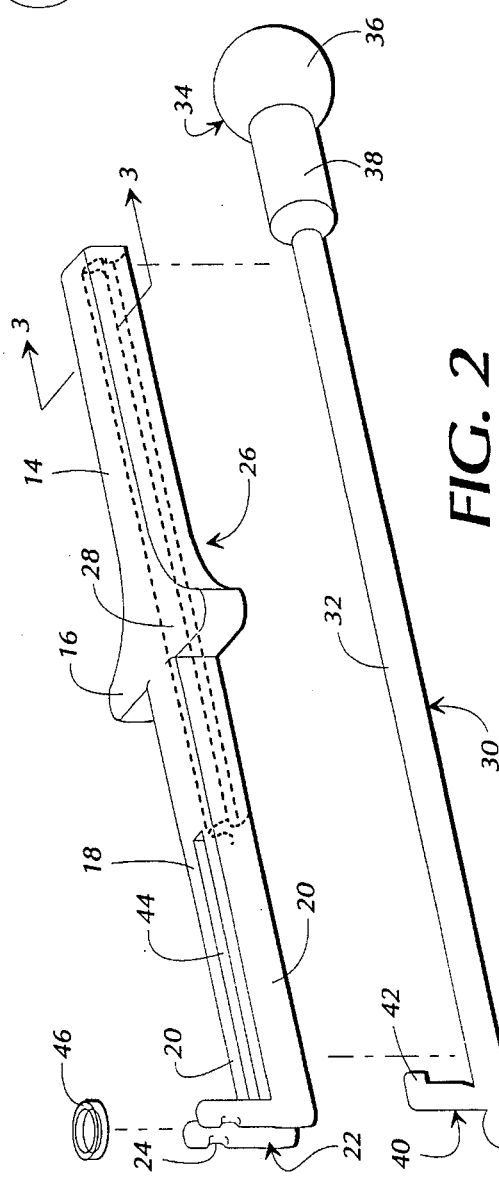
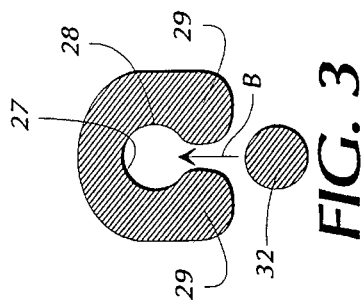
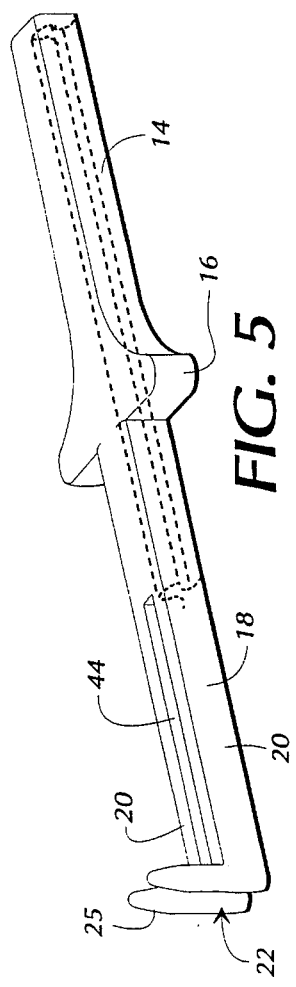

000

ORTHODONTIC TOOL

FIELD OF THE INVENTION

The invention relates generally to orthodontics and dentistry, and more particularly to professional and self care of an orthodontic apparatus. The invention concerns a tool for applying elastic bands onto an orthodontic apparatus.

BACKGROUND OF THE INVENTION

Orthodontics is a branch of dentistry which deals with abnormalities in tooth and jaw positions and relationships which result in facial disharmony and malfunction and unattractive appearance. The objective of orthodontic treatment is to establish normal tooth and jaw position and interrelationship. This is achieved by repositioning the teeth and jaws by the use of mechanical force applied with a fixed or removable apparatus. Often, an orthodontic apparatus is fixed to the teeth, and applies force to the teeth and their supporting structures to produce changes in the relationship of the teeth to each other and to control their growth and development.

A device commonly used in the application of an orthodontic apparatus is an orthodontic elastic, or rubber, band. Such elastic bands are commonly used, and are of great value in the correction of the alignment of the teeth. The elastic band comprises a strong flexible band which can be attached between or within orthodontic apparatus placed upon the upper and/or lower sets of teeth. The band exerts tension upon the orthodontic apparatus and thus the teeth, and gradually corrects the orthodontic deficiency over an extended period of time. The elastic band is typically stretched around two or more hooks projecting from the orthodontic apparatus.

An orthodontic elastic band can lose its rated tension over time, and must be replaced at prescribed intervals. Further, such bands frequently are accidently dislodged and must be replaced for this additional reason. The replacement of an elastic band is not an easy task, and is commonly frustrating and time consuming for both the dental patient and the dentist. In particular, the patient typically needs to apply the elastic band at home, and most often attempts to do so using simply the fingers. As a result, elastic bands are not changed as frequently as they should be, and consequently it can take longer for the teeth to be repositioned.

A few devices have been developed to allow for the comfortable and efficient placement of an elastic band on an orthodontic apparatus. For example, U.S. Pat. No. 4,975,051 to Kargas et al. teaches an instrument for attaching and removing an orthodontic elastic band. This device comprises essentially a single hooked end which will hold an elastic band, attach it over one hook on the orthodontic apparatus and then pull the elastic band and attach it over a second hook of the apparatus. This device, however, does not allow for the simultaneous stretching and placement of the elastic band. Therefore the user must contend with an unstretched and dangling elastic band when placing the first end of the band over the first hook. A second device is taught in U.S. Pat. No. 4,921,423 to Kesling which is entitled "Orthodontic Ligature Gun." This gun, however, is for the placement of an elastic band around a single orthodontic bracket and is not designed for manipulating or stretching the elastic band to stretch it from one hook to another hook.

Thus, it can be seen from the above that a simple tool for enabling the quick and comfortable placement of an elastic band around an orthodontic apparatus is needed.

SUMMARY OF THE INVENTION

It is, therefore, an object of the present invention to provide an inexpensive orthodontic tool for stretching an elastic band and placing the elastic band around an orthodontic apparatus.

It is another object of the present invention to provide a tool for placing an elastic band on an orthodontic apparatus, which tool is easily manipulable with a single hand and is of appropriate size to safely, comfortably and effectively place an elastic rubber band around an orthodontic apparatus within the mouth.

A further object of the present invention is to provide a tool which is manipulable with a single hand, which tool will stretch an elastic band into a triangular shape and allow for placement of the elastic band onto hooks of an orthodontic apparatus in a mouth.

To achieve the foregoing and other objects and in accordance with the purpose of the present invention, a tool is described which facilitates the positioning of an elastic band onto an orthodontic apparatus attached to or about the teeth within the mouth. Preferably, the tool consists of two separatable but interacting elements. These are a body which comprises a handle portion and a tined portion, and a plunger which is slidable within the body. The tined portion has two tines, each of which have an L-shaped end. The plunger also has an L-shaped end, which can be slidably displaced from the tined L-shaped ends. Thus, an elastic band placed over the three ends can be stretched into a triangular shape. The tool is most preferably held and operated by one hand, and is of an appropriate size to be comfortably inserted into the mouth. The tool can be manipulated so that the elastic band stretched upon the three L-shaped ends can be wrapped around the desired hooks of the orthodontic apparatus. The tool is especially designed to be manipulated with one hand, since tools which require the user to use both hands while applying a band on the user's own orthodontics are much more difficult to use effectively.

Preferably the tool is manufactured of an FDA approved plastic or other material. It may be manufactured by an injection molding process and thus may be relatively inexpensive to produce.

Other objects, features and advantages of the present invention will become apparent to one with skill in the art upon examination of the drawings and the detailed description.

BRIEF DESCRIPTION OF THE DRAWINGS

FIG. 2 is an exploded view of the tool showing the interrelationship of the two pieces of the tool.

FIG. 3 is a cross-sectional view of the body portion of the tool taken along lines 3—3 of FIG. 2.

FIG. 4 is a side view representation of a mouth with an orthodontic apparatus attached to the teeth, and showing the operation of the tool.

FIG. 5 is a view of an alternate embodiment of the tool.

DETAILED DESCRIPTION OF THE PREFERRED EMBODIMENT

Figure 1:
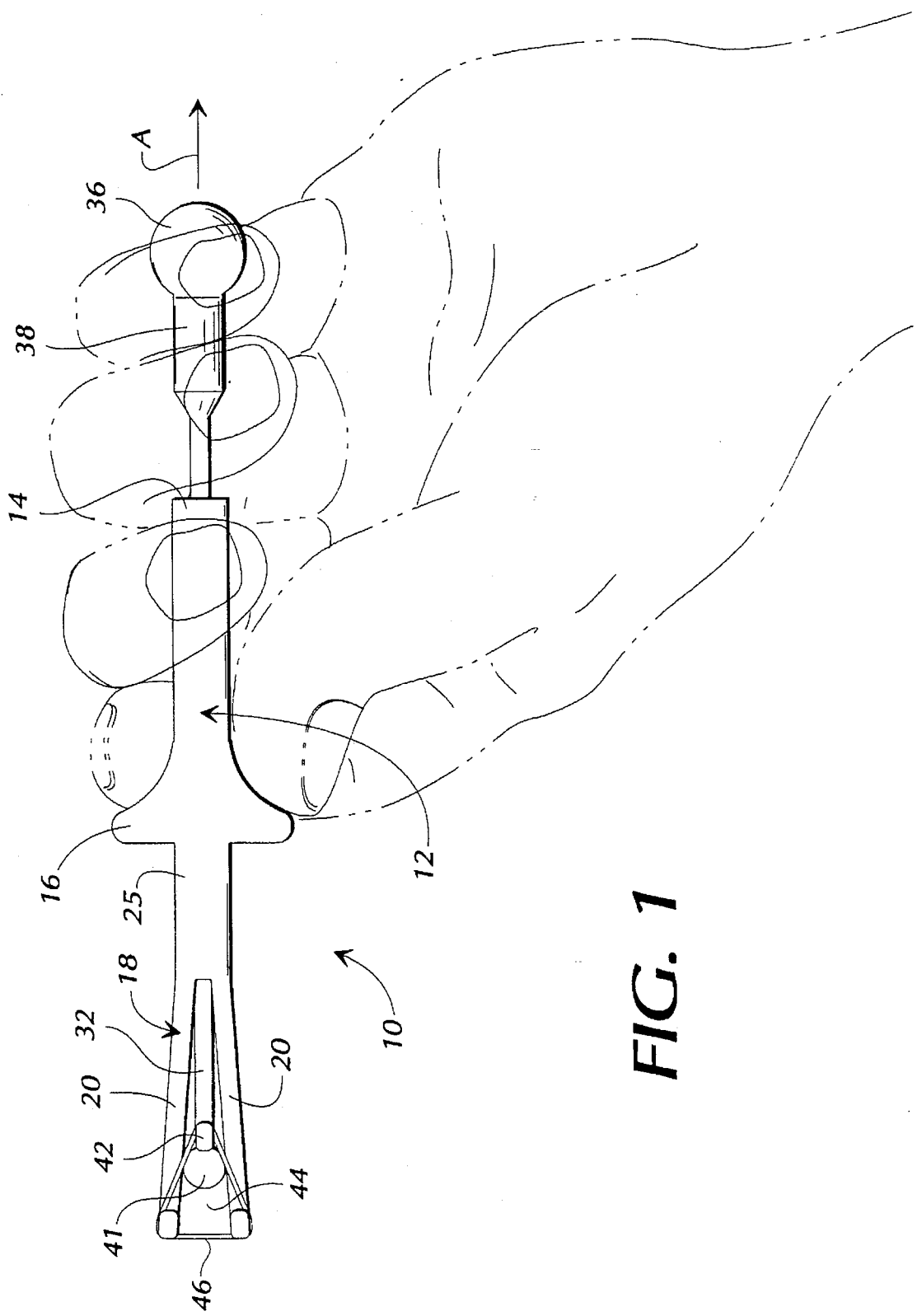
FIG. 1 is a perspective view of the orthodontic tool being correctly held in a person's hand.

FIG. 1 is a perspective view of the invention showing the tool 10 held in the user's hand. The tool consists of a main body 12 which has a handle portion 14, a flanged portion 16, and a tined portion 18. The tined portion comprises two tines 20, each spaced outwardly from one another and having an L-shaped end 22. As shown in FIG. 2, in one embodiment, notch 24 cut into the outward edge of each L-shaped end 22 serves as band retaining means. In a second embodiment, shown in FIG. 5, the band retaining means is a post 25 protruding from each L-shaped end 22. The main body 12 has a rear side 26 and defines a channel 28 which longitudinally extends along body 12, and opens to the rear side 26. FIG. 3 illustrates the channel 28 as being substantially C-shaped, having an inner, substantially circular side wall 27 and two outwardly extending flanges 29. The flanges 29 also extend inwardly to partially close off the channel. It can be seen from FIG. 1 that, in use, the flanged portion 16 of the main body 12 is appropriately placed so that when the handle portion 14 is held in one hand, the thumb and forefinger of that hand can comfortably rest upon the flanged portion 16.

FIGS. 1 and 2 show the second element of the tool, which is a plunger 30 having an elongate shaft 32. Shaft 32 is adopted to be slidably received within the channel 28 of the main body 12. The plunger 30 includes an enlarged end 34 which comprises a ball 36 and a stop portion 38 between shaft 32 and enlarged end 34. The shaft 32 preferably is concentric with stop 38, which is of a diameter larger than that of shaft 32 as shown in FIG. 2. This enlarged end 34 functions to provide a handle for griping the plunger to that the plunger thereafter can be slid within the channel 28. In use, as shown in FIG. 1, the last two fingers away from the thumb of the hand holding the tool can pull on the last ball 36 in the direction of the arrow A. The stop 38 of the plunger functions to stop any movement of the plunger through the channel in the direction away from arrow A when stop 38 abuts handle 14.

The opposite end of the plunger 30 comprises a third L-shaped end 40 which is tipped with a hook 42 extending inwardly. Plunger 30 is slidably received within channel 28 of body 12 by forcing shaft 32 laterally between flanges 29 and toward channel 28, as shown in FIG. 3. Since the elements preferably are plastic, having some elasticity, flanges 29 move apart by the camming action of shaft 32 moving toward side wall 27 in the direction of arrow B. When shaft 32 is received within channel 28, which is sized slightly larger than shaft 32, flanges 29 return to their usual positions toward one another, and releasably retain shaft 32 within channel 28, while allowing the shaft to slide freely within the channel. When the shaft is received within the channel, the third L-shaped end 40 is positioned with the groove 44 formed between the two tines 20. At the junction of end 40 with shaft 32 is spreader 41 which slides down groove 44 and functions to spread apart tines 20 as the plunger 30 is moved within channel 28 by a camming action against the sides of tines 20. The groove 44 extends only partially down the length of the body 12 as shown in FIG. 1, so that the plunger 30 is stopped in its movement at a predetermined point down the shaft, that is at the junction of the opposing tines 20. Thus, an elastic band 46 placed around the three L-shaped ends can be extended and spread apart by sliding the plunger 30 down the channel 28, thus moving the third L-shaped end 40 away from the first and second L-shaped ends 22. Thus, the elastic band 46 is stretched into a triangular shape between the respective L-shaped ends. The retaining means on the first two L-shaped ends and the tooth 42 on the third L-shaped end serve to prohibit the elastic band 46 from being expelled off of the L-shaped ends before desired.

The tool of the present invention is preferably manufactured from an FDA approved plastic or other material. An example of such plastic is polyethylene. The tool is preferably manufactured by an injection molding procedure but can be manufactured by any desired procedure. The two pieces of the tool typically are manufactured separately and assembled, as referenced above, at the point of manufacture.

In operation, the user, either the dental patient or the professional, first places an elastic band over the three aligned, substantially parallel L-shaped ends. The user then grasps the tool in either the right or left hand, and holds the tool so that the thumb and forefinger rest upon the flanged portion 16 of the tool. The remaining three fingers are then used to grasp the exploded portion 34 of the plunger 30, and at least the two fingers furthest away from the thumb pull the handle 34 away from the body 12, thus pulling the third L-shaped end 40 down through the groove 44 formed by the two tines 20 and away from the first and second L-shaped ends 22. The spreader 41 causes the tines 20 to slightly spread apart. In this way, the elastic band 46 is stretched into a triangular shape.

Holding the elastic band in its stretched position, the user inserts the tool 10 into the mouth, and places the elastic band portion between the two tines 20 over the first hook 48 of the orthodontic apparatus 50. When the elastic band 46 is secured over the first hook 48, the first and second L-shaped ends 20 can be disconnected from the elastic band 46 by a slight turning of the entire tool 10. The other end of the elastic band 46 is still held by the third L-shaped end 40 and the hook 42, and the elastic band is thus pulled and placed over the second hook 52 of the orthodontic apparatus. At this point, the third L-shaped end 40 is disconnected from the elastic band 46 and the tool is removed from the mouth leaving the elastic band 46 in its desired position around the two hooks 48 and 52 of the orthodontic apparatus.

It will further be obvious to those skilled in the art that many variations may be made in the above embodiments here chosen for the purpose of illustrating the present invention, and full result may be had to the doctrine of equivalents without departing from the scope of the present invention, as defined by the appended claims.

What is claimed is:

1. An orthodontic tool for placing an elastic band on an orthodontic apparatus in a mouth, comprising:

a shaft having a handle portion and a tined portion and wherein the tined portion has two tines having first and second L-shaped ends;

a channel running the length of the shaft;

a plunger slidably engaged in the channel;

said plunger having a third L-shaped end which slides between said two tines; and a spreader on the third L-shaped end which spreads the two tines apart from one another as the third L-shaped end is slid away from the first and second L-shaped ends;

so that an elastic band placed around the three L-shaped ends can be stretched into a substantially rectangular shape by sliding the third L-shaped end away from the first and second L-shaped ends.

2. The orthodontic tool of claim 1 and further comprising means for temporarily retaining the position of the elastic band on the three L-shaped ends.

3. The orthodontic tool of claim 2 wherein the retaining means comprises a notch cut into the outer edge of each L-shaped end of the two tines and an inwardly extending tooth on the tip of the L-shaped end of the plunger.

4. The orthodontic tool of claim 2 wherein the retaining means comprise a post extending from each L-shaped end of the two times and an inwardly extending tooth on the tip of the plunger L-shaped end.

5. The orthodontic tool of claim 1 and further comprising a flanged portion of the shaft intermediate the handle portion and the tined portion whereby when the tool is grasped in one hand by the handle the thumb and forefinger rest upon the flanged portion.

6. The orthodontic tool of claim 1 and wherein the plunger has a second end which comprises an exploded portion such that the exploded portion serves as a means to grasp the plunger and slide the plunger within the channel.

7. An orthodontic tool for placing an elastic band on an orthodontic apparatus within a mouth, comprising:

a shaft having a handle portion, a tined portion, and a flanged portion intermediate and having a front side and a rear side;

a channel running the length of the shaft with its opening towards the rear side of the shaft;

wherein the tined portion comprises two tines each having an L-shaped end, and each L-shaped end having a post extending from its tip;

a plunger having an elongate shaft which slidingly engages said channel, said plunger having one exploded end and the other end being L-shaped and tipped with an inwardly extending tooth; and a spreader on the plunger L-shaped end which functions to spread apart the tines as the plunger is pulled through the channel;

wherein the plunger L-shaped end slides between the tines when the plunger is slid along the channel;

so that when the user grasps the tool by the handle portion and pulls down on the plunger by pulling on the exploded end, the plunger L-shaped end slides between the tines and an elastic band attached around the three L-shaped ends is stretched into a triangular shape and the user can attach the elastic band over the orthodontic apparatus within the mouth.

8. The orthodontic tool of claim 7 wherein the exploded tip of said plunger comprises a ball portion and a stop portion wherein the stop portion prevents the plunger from extending into the shaft further than would maintain a substantially parallel position of the three L-shaped ends.

9. The orthodontic tool of claim 7, wherein the groove formed by the two tines extends only so far down the length of the shaft and the L-shaped end of the plunger is able to travel only a predetermined distance so that the elastic band wrapped around the three L-shaped ends is able to extend only to a predetermined distance.

10. The orthodontic tool of claim 7 wherein the channel is a substantially C-shaped channel having a middle substantially circular portion and two ends which slightly close off the opening, thereby keeping the plunger in place within the channel.

* * * * *